United States Patent [19]

Pozzi

[11] 4,307,196
[45] Dec. 22, 1981

[54] FERMENTER OF REACTOR FOR ZOOTECHNIC LIQUID MATERIALS

[75] Inventor: Vladimiro Pozzi, Bagnolo in Piano, Italy

[73] Assignee: Giza S.p.A., Italy

[21] Appl. No.: 147,547

[22] Filed: May 5, 1980

[30] Foreign Application Priority Data

May 9, 1979 [IT] Italy ................................. 22489 A/79

[51] Int. Cl.³ .............................................. C12M 1/02
[52] U.S. Cl. ................................. 435/316; 261/36 R; 366/88; 366/323; 435/315; 435/818
[58] Field of Search ............... 435/316, 315, 307, 801, 435/813, 818; 261/36 R, 77, 91; 366/88, 323

[56] References Cited

U.S. PATENT DOCUMENTS

| Re. 28,901 | 7/1976 | Kim .................................. 366/88 X |
| 2,244,902 | 6/1941 | Stich ................................ 435/316 X |
| 2,530,814 | 11/1950 | De Becze et al. ............... 435/315 X |
| 2,926,619 | 3/1960 | Kruder .................................. 366/88 |
| 3,019,895 | 2/1962 | Loeuenstein et al. .......... 366/323 X |
| 3,085,288 | 4/1963 | Street .............................. 366/323 X |
| 3,495,813 | 2/1970 | Marenghi et al. ................ 261/91 X |
| 3,852,384 | 12/1974 | Bearden ............................... 261/77 |
| 4,063,718 | 12/1977 | Koch ................................ 366/88 X |
| 4,145,383 | 3/1979 | Randall ......................... 261/36 R X |

FOREIGN PATENT DOCUMENTS

| 994354 | 6/1965 | United Kingdom . |
| 1112682 | 5/1968 | United Kingdom . |
| 1435690 | 5/1976 | United Kingdom . |
| 1529777 | 10/1978 | United Kingdom . |

*Primary Examiner*—Robert J. Warden
*Attorney, Agent, or Firm*—Anthony H. Handal

[57] ABSTRACT

A fermenter or reactor for zootechnic liquid materials, comprising a fermentation vessel or container, having positioned therein a movable member for the mixing and stirring of the liquid material. In the reactor or fermenter, said member comprises at least one substantially vertical tube or pipe having windows or slots formed therein as distributed along the length thereof; within said tube or pipe an Archimedean screw is housed and rotatable about its own axis through the action of a drive member.

Such a fermenter or reactor is suitable to ensure an accurate mixing of the fermenting mass, while slowly stirring the latter and bringing all of the mass particles in contact with the microbic flora without any disturbance to the fermentation cycle.

9 Claims, 2 Drawing Figures

FERMENTER OF REACTOR FOR ZOOTECHNIC LIQUID MATERIALS

This invention relates to a fermenter or reactor for zootechnic liquid materials, particularly for bovine and swine liquid materials. In order to recover combustible gases and fertilizing muds and accordingly to reduce the pollution deriving from the use thereof as such, the zootechnic liquid materials are subjected to anaerobic fermentations in fermenters or reactors, wherein such liquid materials are maintained for predetermined periods of time at controlled temperatures and are stirred.

Stirring of liquid materials in fermenters or reactors has the function of moving the whole mass of liquid materials in order to bring each of the particles in contact with the microbic flora and permit degassing of such a mass, that is to facilitate the release of gases (mostly comprising methane gas) developed during fermentation. Therefore, such a stirring of the fermenting liquid material mass should be complete and accurate, but cannot be violent or excessive as it would disturb the fermentation cycle, either slowing or entirely stopping it.

Additionally, it should be taken into account that zootechnic liquid materials are very thick and that a fertilizing mud tends to be separated therefrom; finally, layers of material having different specific gravity are formed in the fermenter or reactor, which should be prevented as far as possible, while avoiding an excessive mixing for the above disclosed reasons.

To mix a fermenting liquid material, common blade stirrers were tried, but the results were disappointing: a liquid material could be maintained substantially uniform and accurately mixed, only by vigorously stirring it to such an extent as to damage or impair the fermentation thereof.

It is the object of the present invention to provide a fermenter or reactor, particularly for fermentation of zootechnic liquid materials, which is provided with means for accurately mixing the liquid material mass, while slowly stirring it, bringing all of the liquid material particles in contact with the microbic flora without any disturbance to the fermentation cycle and allowing an optimum degassing of the mass.

It is another object of the invention to provide a fermenter or reactor of the above mentioned type, which is of simple structure and low cost of manufacture and operation.

These and still further objects are accomplished by a fermenter or reactor, accomodating therein at least one substantially vertical tube or pipe, in which windows or slots are formed as distributed along the length of said tube or pipe, an Archimedean screw being housed within such a tube or pipe and connected to a rotation driving motor.

In order that the structure and characteristics of a fermenter or reactor according to the invention be more clearly understood, a preferred embodiment thereof will now be described merely by way of example with reference to the accompanying drawings, in which.

Figure 1:
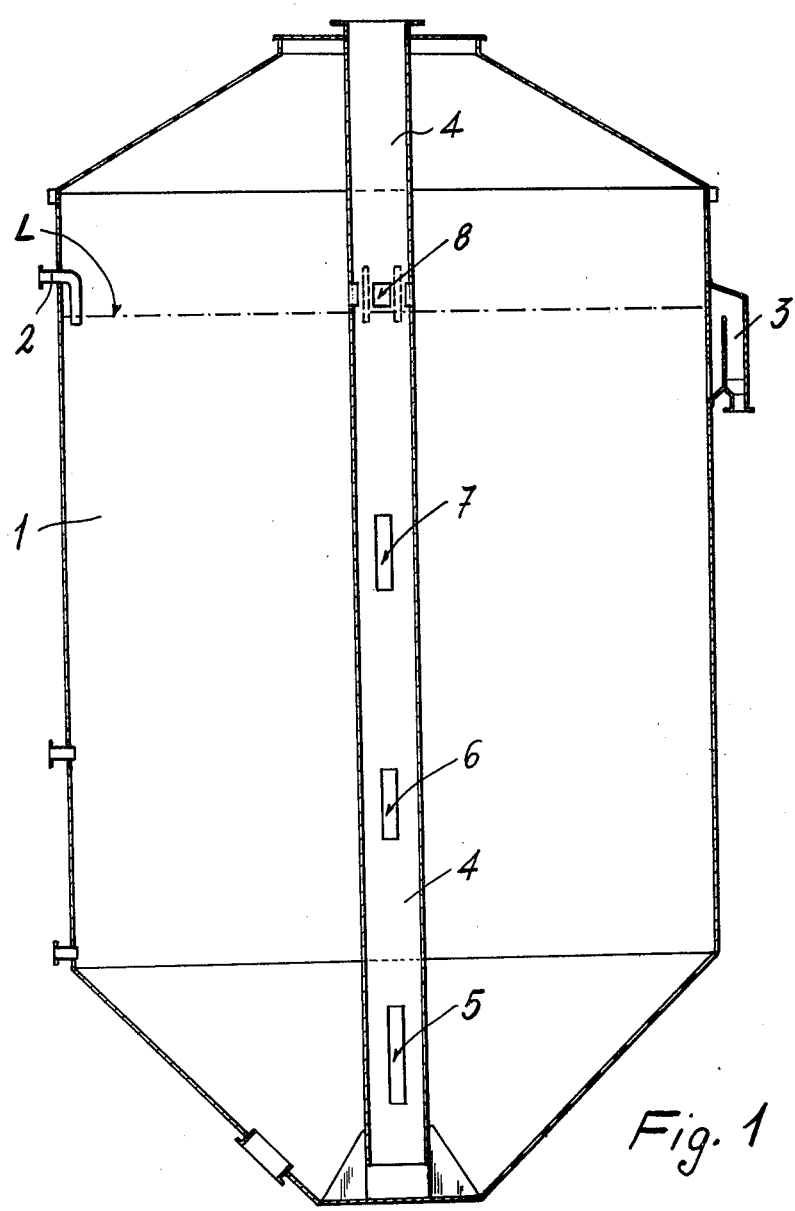
FIG. 1 is a diagrammatic axial sectional view of a fermenter or reactor.

Referring first to FIG. 1, in which a fermenter or reactor for zootechnic liquid materials has been outlined, as comprising a vessel or container 1, provided with an opening 2 for the liquid material inlet, an opening 3 for the discharge of fertilizing muds, and circulation openings, etc., which have not been numbered on the drawing for the sake of simplicity. The liquid material in the fermenter or reactor reaches the level shown by the dash-dot line L.

Within the fermenter or reactor and coaxially therewith a tube or pipe 4 is mounted, in which several groups of windows or slots are formed (each group comprising three different windows or slots which are equal and equispaced to each other) denoted by reference numerals 5, 6, 7 and 8. As it will seen from the drawing, windows or slots 5 are of larger length and width than the others, and windows or slots 8 are located just at a higher level than the liquid material level L in the fermenter or reactor. It can also be seen from the drawing that the groups of windows or slots 5, 6, 7 and 8 are substantially equally spaced from one another, and more particularly it will be seen that the distance or spacing separating one group of windows or slots from a group adjacent thereto is about ¼th of the length of said tube or pipe 4.

Figure 2:
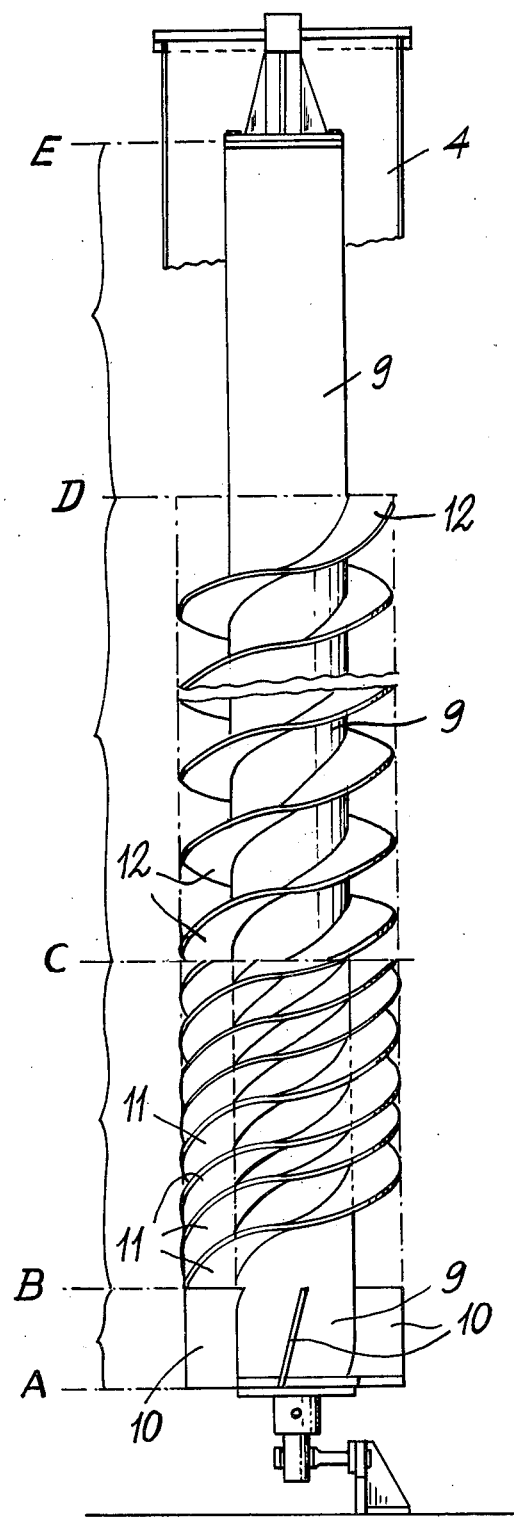
FIG. 2 is a diagrammatic axial elevational view of an Archimedean screw comprising the mixing and stirring for the liquid material contained in the fermenter or reactor.

This tube or pipe 4 accomodates therein an Archimedean screw which has been separately outlined in FIG. 2.

The Archimedean screw has a somewhat peculiar structure. At its lower portion (in the section A-B shown by brace parenthesis) from a cylindrical trunk 9, there radially project four blades inclined by about 10°–15° relative to the vertical; followed (section B-C) by a zone where the Archimedean screw comprises a four start helix 11 (that is four spirals disposed around the trunk 9): then (section C-D), the screw is formed of a two start helix 12 (that is two side by side spirals disposed around the trunk 9); finally, in section D-E no helixes project from trunk 9.

While the blades 10 are restricted to the lower portion of said Archimedean screw, it should be appreciated that the separation zone (Zone C) of helixes 11 from helixes 12 is positioned at said windows or slots 5, while the helixes 12 extend to above the windows or slots 8. It should then be pointed out that the Archimedean screw is connected to a driving motor (not shown) and that the diameter of tube or pipe 4 is much less than that of vessel or container 1.

For example, it was found that a fermenter or reactor for zootechnic liquid materials could have the following characteristics: vessel or container 1 with a diameter of 6.5 m, a total height of 12 m; tube or pipe 4 with a diameter of 0.5 m and height of about 12 m; windows or slots 5 having a length of 1 m and width of 0.2 m; windows or slots 6 and 7 having a length of 0.75 m and width of 0.18 m; windows or slots 8 having a length and width of 0.30 m; blades 10 of the Archimedean screw axially extending for 20 cm; length of the Archimedean screw section B-C of 1.3 M where the spirals or helixes 11 are of four start type; and length of section C-D of 7.8 m, where the Archimedean screw helixes are of two start type.

During the liquid material fermentation (which may last from 10 to 20 days, at a temperature ranging between 30° and 40° C., preferably 35° C.), the Archimedean screw is rotated at a speed ranging between 30 and 120 r.p.m., preferably at about 70 r.p.m. The liquid material in the fermenter or reactor is very thick and has the tendency of having the greatest thickness at the bottom of vessel or container 1. The blades 10 perform the function of scraping the material at the bottom of tube or pipe 4, but more important is the characteristic of the difference in number of starts for helixes 11 and 12 in the Archimedean screw sections B-C and C-D, respectively.

Thus, at the lower portion of vessel or container 1, the liquid material is very thick and the four start helixes 11 are such as to vigorously mix it. Should the Archimedean screw be of four starts also in the section C-D, at which the liquid material is less thick, such an Archimedean screw would cause a too vigorous and fast mixing of the liquid material, compromising the fermentation. This is the reason why the Archimedean screw has in section C-D helixes 12 of only two starts. Thus, as the Archimedean screw rotates, the four start helixes 11 vigorously and at a higher speed move the thicker liquid material, while the two start helixes 12 more smoothly move the overlying portion of the liquid material. The liquid material withdrawn by the blades 10 and accordingly by the helixes 11 at the bottom of tube or pipe 4 is caused to move fast and at large flow rate up along said tube or pipe 4: since this amount of liquid material is larger than that which can be transported by the helixes 12 of only two starts, the excess portion of liquid material is ejected through the windows or slots 5 of tube or pipe 4. As a matter of fact, at the lower portion or bottom of the reactor, the thickest portion of the liquid material is cycled by entering at the lower end of tube or pipe 4, moving up along said tube and being mostly ejected at the lower portion or bottom of windows 5.

In turn, the Archimedean screw helixes 12 causes a suction of liquid material at the upper portions of windows 5, 6 and 7 and ejection of liquid material from tube 4 through the lower portions of windows 6, 7 and 8. Thus, the Archimedean screw creates in the liquid material volume or mass in the reactor a turbulence which is sufficiently vigorous to bring the liquid material particles in contact with the microbic flora, but sufficiently smooth not to disturb the fermentation, at the same time allowing the development of the combustible gases (mostly methane) being formed during fermentation. Experiments that have been carried out proved that optimum results in fermentation of zootechnic liquid materials are only possible if such liquid materials are mixed by an Archimedean screw, such as that described.

As apparent, an Archimedean screw instead of comprising successive sections of helixes having different number of starts could also comprise a constant number of starts, but of varying pitch, that is with a shorter pitch at the lower end of the Archimedean screw that at the higher section of such an Archimedean screw.

What we claim is:

1. A fermentation reactor for zootechnic liquid material, comprising a fermentation vessel for containing the liquid material to be processed by the reactor, a tube contained within the vessel and positioned therein with a substantially vertical orientation, said tube defining a plurality of slots along its length, said slots having a generally elongated shape and having a width and a length much greater than said width, said slots being oriented on said tube with their lengths substantially aligned with the axis of said tube, an Archimedean screw contained within said tube, said screw being positioned with its axis substantially in coincidence with the axis of said tube, said screw having an upper portion and a lower portion, the lower portion of said screw comprising material handling surfaces positioned, configured and dimensioned to convey a larger volume of liquid when said screw is rotated at a given speed than the volume of liquid which the upper portion of said screw conveys at said given speed, and scraping blade means projecting outwardly from said lower portion of said screw and inclined with respect to the axis of said screw.

2. A fermentation reactor as in claim 1 wherein said slots are distributed in groups spaced apart from one another along the axis of the tube.

3. A fermentation reactor as in claim 2 further comprising drive means for rotating said screw about its own axis.

4. A fermentation reactor as in claim 2 wherein the number of helix starts in the lower portion of the screw is greater than the number of helix starts in the upper portion of the screw.

5. A fermentation reactor as in claim 2 wherein the helix pitch in said lower portion of said screw is smaller than the helix pitch in said upper portion of said screw.

6. A fermentation reactor as in claims 4 or 5 wherein said scraping blades are inclined at an angle in the range from about 10° to about 15° with respect to the axis of the Archimedean screw.

7. A fermentation reactor as in claim 2 wherein each group of slots consists of at least three identical slots equi-spaced around the perimeter of the tube.

8. A fermentation reactor as in claims 2 or 7 wherein the distance separating each group of slots from the next adjacent group of slots is about one-fourth the length of the tube.

9. A fermentation reactor as in claims 1, 2 or 7 wherein the slots at the lowermost end of said tube have a length and a width greater than the length and the width of the other slots on said tube.

* * * * *